United States Patent [19]

McNeely et al.

[11] Patent Number: 5,458,583
[45] Date of Patent: Oct. 17, 1995

[54] GASTROSTOMY CATHETER SYSTEM

[75] Inventors: Gwyn F. McNeely, Gainesville, Fla.; Christine Decaria, Sunnyvale; Stephen Parks, Redwood City, both of Calif.

[73] Assignee: Medical Innovations Corporation, Milpitas, Calif.

[21] Appl. No.: 289,841

[22] Filed: Jun. 12, 1994

Related U.S. Application Data

[63] Continuation of Ser. No. 1,271, Jan. 7, 1993, abandoned.

[51] Int. Cl.$^6$ .................................................. A61M 29/00
[52] U.S. Cl. ........................................... 604/96; 604/101
[58] Field of Search ............... 604/96, 101; 606/191–194

[56] References Cited

U.S. PATENT DOCUMENTS

| | | | |
|---|---|---|---|
| 4,057,065 | 11/1977 | Thow | 604/101 |
| 4,453,545 | 6/1984 | Inoue | 604/101 |
| 4,666,433 | 5/1987 | Parks . | |
| 4,701,163 | 10/1987 | Parks . | |
| 4,705,401 | 11/1987 | Kim | 128/343 |
| 4,758,219 | 7/1988 | Sacks et al. . | |
| 4,798,592 | 1/1989 | Parks . | |
| 4,819,664 | 4/1989 | Nazari | 604/96 |
| 4,832,028 | 5/1989 | Patel | 606/194 |
| 4,846,174 | 7/1989 | Willard | 604/96 |
| 4,863,438 | 9/1989 | Gauderer et al. . | |
| 4,867,742 | 9/1989 | Calderon | 604/101 |
| 4,911,163 | 3/1990 | Fina | 604/101 |
| 4,944,732 | 7/1990 | Russo . | |
| 4,981,482 | 1/1991 | Ichikawa | 606/191 |
| 5,007,900 | 4/1991 | Picha et al. . | |
| 5,059,178 | 10/1991 | Ya | 604/101 |
| 5,071,405 | 12/1991 | Piontek et al. | 606/96 |
| 5,073,166 | 12/1991 | Parks et al. . | |
| 5,074,846 | 12/1991 | Clegg et al. . | |
| 5,080,650 | 1/1992 | Hirsch et al. . | |
| 5,084,014 | 1/1992 | Picha et al. . | |
| 5,102,390 | 4/1992 | Crittenden et al. | 606/194 |
| 5,112,310 | 5/1992 | Grobe . | |
| 5,123,914 | 6/1992 | Cope . | |
| 5,151,086 | 9/1992 | Duh et al. | 604/96 |
| 5,158,543 | 10/1992 | Lazarus | 606/191 |
| 5,167,627 | 12/1992 | Clegg et al. | 604/96 |
| 5,180,367 | 1/1993 | Kontos et al. | 606/194 |
| 5,234,454 | 8/1993 | Bangs | 606/191 |

OTHER PUBLICATIONS

Medi-tech, Incorporated, "Instructions For Use TractMaster™ Balloon Dilatation Catheters," Rev. Jul. 1985.

Primary Examiner—John D. Yasko
Assistant Examiner—Manuel Mendez
Attorney, Agent, or Firm—Workman Nydegger Seeley

[57] ABSTRACT

A system and method for inserting a gastrostomy catheter through a passageway formed through the abdominal and stomach walls of a patient. The gastrostomy catheter is mounted onto a dilatation catheter with a dilatation member such as an inelastic balloon on the distal extremity thereof. An introducer needle is first advanced through the walls of the patient's abdomen and stomach into the interior of the stomach and then a guidewire is advanced through the inner lumen of the needle into the stomach interior. The gastrostomy catheter-dilatation catheter assembly is advanced over the guidewire until the balloon on the dilatation catheter is in proper position crossing both the abdominal and gastric walls. Upon inflation of the balloon on the dilatation catheter, the passageway is expanded enough so that the gastrostomy catheter can be advanced therethrough to dispose the distal end of the gastrostomy catheter within the interior of the stomach. The balloon on the distal end of the gastrostomy catheter is inflated so as to form an internal retention member and the catheter withdrawn in order to urge the inflated balloon against the stomach wall. Preferably, the gastrostomy catheter has an external retention ring on the shaft thereof which is slid against the exterior of the patient's abdomen to seal the passageway through the abdominal wall.

13 Claims, 5 Drawing Sheets

GASTROSTOMY CATHETER SYSTEM

This application is a continuation of U.S. application Ser. No. 08/001,271, filed Jan. 7, 1993 and now abandoned, for GASTROSTOMY CATHETER SYSTEM.

BACKGROUND OF THE INVENTION

This invention generally relates to enteric feeding tubes and particularly to enteric feeding tubes which are inserted into the interior of a patient's stomach through the patient's abdominal and stomach walls.

There are a number of patient's who are unable to chew or swallow for relatively long periods of time. Examples of such patient's include those who are neurologically impaired, e.g. stroke, those who have had traumatic injury to their head or neck areas. e.g. a broken jaw, and those who have an obstruction in their esophagus, e.g. cancer. In these instances, it is common practice to insert an enteric feeding tube, sometimes called a gastrostomy tube or catheter, through the patient's abdominal and gastric walls into the interior of the patient's stomach in order to feed the patient nutrients, medicaments and the like through the gastrostomy tube until such time of the patient can chew and swallow on his or her own.

There are several well known techniques for inserting a gastrostomy tube into a patient's stomach for enteral feeding and medication. One of such techniques involves making an opening in portions of the stomach wall and the abdominal wall and passing the gastrostomy tube through the opening until its distal end is well disposed within the patient's stomach. Very frequently in this technique the stomach wall is secured to the abdominal wall by means of a plurality of T-fasteners. The opening in the abdominal and stomach walls may be formed by means of a Seldinger technique wherein a relatively large needle is inserted through the walls into the stomach, a guidewire or a peel-away introducer sheath, such as shown in U.S. Pat. No. 4,166,469 is inserted through the needle forming the opening and then the needle is removed. The opening is usually enlarged to allow for the passage of the gastrostomy tube by advancing a series of dilators of increasing diameters through the opening.

However, it is not uncommon to experience some difficulty in advancing the dilators and a gastrostomy tube through the opening formed in the patient's abdominal and stomach walls. If the stomach wall is secured to the abdominal wall by T-fasteners, sometimes the forces applied to the stomach wall by the advancing dilators or gastrostomy tube are sufficiently high to cause the stomach wall to tear away from the T-fasteners which secure the stomach wall to the abdominal wall. If the stomach wall is not secured to the abdominal wall, the stomach wall tends to be pushed away by the dilators. i.e. forming a tent-like indentation in the stomach wall.

What has been needed is a system which can easily advance a gastrostomy tube through the patient's abdominal wall and stomach wall so that the distal end thereof is properly disposed within the patient's stomach without damage to the patient's stomach wall. These and other needs are satisfied by the present invention.

SUMMARY OF THE INVENTION

This invention is directed to a catheter system for placing a gastrostomy catheter into the interior of a patient's stomach through the secured walls of the patient's stomach and abdomen.

The system of the invention includes a dilatation catheter having an elongated catheter shaft with an expandable dilatation member, e.g. an inflatable balloon on a distal section of the catheter shaft. If an inflatable member is provided, the catheter has an inflation lumen which is in fluid communication with the inflatable member. An adapter is provided on the proximal end of the catheter shaft which is adapted to direct inflation fluid from a source to the inflation lumen in the catheter shaft. The dilatation catheter has an outer diameter which is small enough to be slidable within an inner lumen of a gastrostomy catheter and it is long enough so that the proximal end of the dilatation catheter extends out of the proximal end of the gastrostomy catheter while the dilatation balloon on the distal section of the dilatation catheter extends completely out of the distal end of the gastrostomy catheter. The adapter on the proximal end of the dilatation catheter is preferably removable to allow the gastrostomy catheter to be more easily loaded onto the proximal end of the dilatation catheter. The dilatation catheter may be provided with a guidewire lumen which extends to a guidewire port in the distal end of the catheter to facilitate guiding the catheter through over a guidewire the passageway formed in the abdominal and gastric walls to be dilated.

The balloon of the dilatation catheter is formed of a polymer material which inflates to a desired diameter but which does not expand significantly beyond that the desired diameter for dilatating a passageway for the gastrostomy catheter, even when the inflation pressure is increased significantly beyond the pressure which expands the balloon to the desired diameter, i.e. the balloon is relatively inelastic or noncompliant at the elevated pressures. Suitable balloon materials include inelastic polymers such as polyethylene, polyethylene terephthalate, polyvinyl chloride and polyolephinic ionomers such as Surlyn®.

The gastrostomy catheter generally has a catheter shaft with a first lumen extending from the proximal end to the distal end of the catheter shaft which is adapted to direct fluids from the proximal end of the catheter, out the port in the distal end into the interior of the patient's stomach. The gastrostomy catheter is also provided with an internal retention means which prevents the removal of the catheter through the passageway extending through the abdominal and gastric walls. Preferable, the internal retention means is an expandable member such as a balloon or a mechanical device as described in U.S Pat. No. 4,666,433 and U.S. Pat. No. 5,073,166, which are incorporated herein by reference. Both of these patents have been assigned to the present assignee Medical Innovations Corp. of Milpitas, Calif. With a catheter having an inflatable member, a second lumen extends within the catheter shaft from the proximal end of the gastrostomy catheter to the interior of the balloon to provide fluid for the latter's inflation after the distal extremity of the gastrostomy catheter is properly disposed within the patient's stomach.

Presently preferred embodiments of the gastrostomy catheter are described in U.S. Pat. No. 4,685,592, U.S. Pat. No. 4,701,163 and U.S. Pat. No. 4,798,592, which are incorporated herein by reference thereto. As described in these patents, the balloon on the distal section of the gastrostomy catheter is inflated while it is disposed within the interior of the stomach and then the catheter is tugged to pull the inflated balloon against the interior of the stomach wall. An exterior retention ring, which is frictionally mounted onto the shaft of the gastrostomy catheter, is then urged along the catheter shaft until it presses against the exterior surface of the abdominal wall to ensure that the gastrostomy catheter is secured and can not move distally.

The dilatation catheter, which is adapted to be disposed within the fluid delivery lumen of the gastrostomy catheter, is advanced into the passageway formed through the abdominal and stomach walls until the dilatation balloon extends along the entire length of the passageway and, once properly positioned within the passageway, the balloon is inflated to dilate the passageway. The dilatation is preferably performed under fluoroscopic observation. During the initial stage of the balloon inflation, a portion of the dilatation balloon within the passageway, particularly within the fascia of the abdominal wall does not expand completely, thus forming a waist which is readily seen fluoroscopically if the balloon is inflated with radiopaque fluid. The inflation pressure within the dilatation balloon is increased until the diameter of the inflated balloon is essentially the same along its length, i.e. the waist disappears. More than one inflation may be required for complete dilatation. After the dilatation balloon is deflated, the gastrostomy catheter may be advanced over the dilatation catheter until the distal end of the gastrostomy catheter is disposed well within the interior of the patient's stomach. Preferably, the gastrostomy catheter is mounted over the proximal end of the dilatation catheter onto the shaft thereof before the dilatation catheter is inserted into the passageway in the abdominal wall and the gastric wall so that when the passageway is dilated, the dilatation balloon can be deflated and the gastrostomy catheter immediately advanced thereover.

Once the distal end of the gastrostomy is disposed well within the interior of the stomach, the dilatation catheter may then be removed. To secure the distal end of the gastrostomy catheter the balloon on the distal end of the gastrostomy catheter within the stomach is inflated and the catheter withdrawn through the passageway in the abdominal and stomach walls until the inflated balloon is urged snugly against the interior of the stomach wall. A sealing ring which is frictionally mounted on the shaft of the gastrostomy catheter is then advanced distally on the shaft until it is pressed against the exterior of the abdominal wall. This procedure seals the passageway.

The present invention provides a catheter system which facilitates the placement of a gastrostomy catheter within a patient's stomach. The inflation of the dilatation balloon on the dilatation catheter applies essentially only radial pressure against the passageway through the patient's abdominal and stomach walls to expand the passageway sufficiently to allow for the passage therethrough of a gastrostomy tube. However, the expansion of the passageway and the passage of the gastrostomy catheter therethrough applies little or no shear forces to the stomach wall which can cause damage, e.g. tearing the stomach lining away from T-fasteners which secure the stomach wall to the abdominal wall. These and other advantages of the invention will become more apparent from the following detailed description of the invention, when taken in conjunction with the accompanying exemplary drawings.

DETAILED DESCRIPTION OF THE INVENTION

Figure 1:
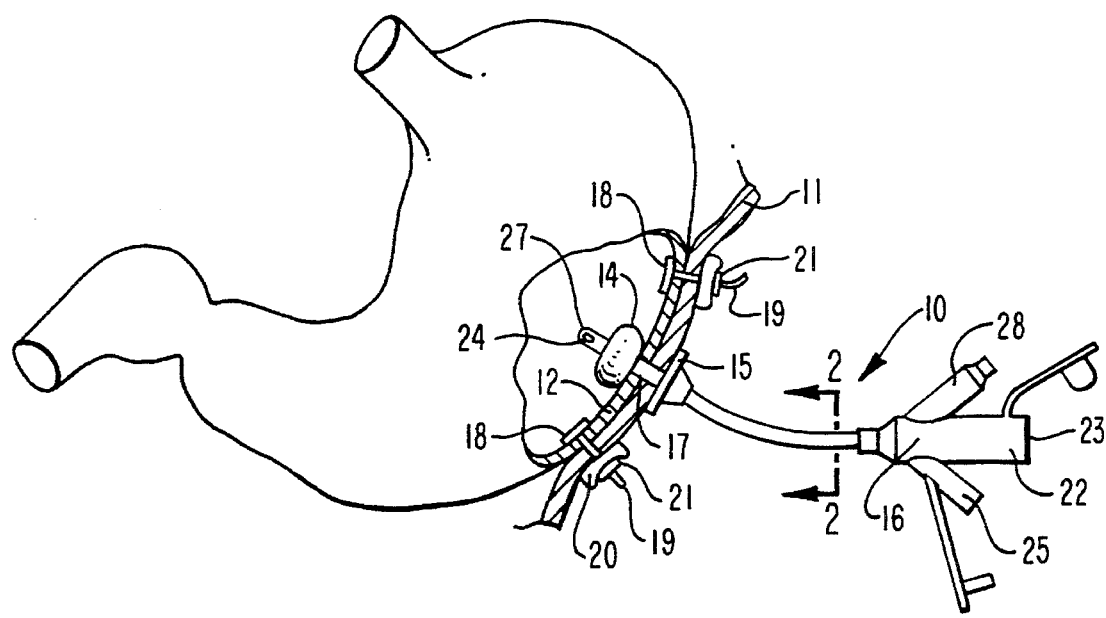
FIG. 1 is an elevational view, partially in section, of a gastrostomy catheter disposed through a passageway in a patient's abdominal and stomach walls.
Figure 2:
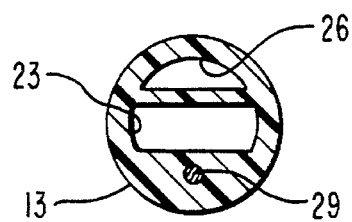
FIG. 2 is a transverse cross-sectional view of the catheter shown in FIG. 1 taken along the lines 2—2.

FIGS. 1 and 2 depict a gastrostomy catheter 10 extending through a patient's abdominal wall 11 and stomach wall 12. The gastrostomy catheter 10 has an elongated catheter shaft 13 with an internal retention member, inflatable balloon 14 on a distal portion thereof, an external retention ring 15 fictionally mounted onto the exterior of the shaft 13 and a multiarm adapter 16 on the proximal end of the catheter shaft. As shown, the balloon 14 is inflated and the catheter 10 is withdrawn through the passageway 17 until the balloon is urged against the inside of the stomach wall 12. The external retention ring 15 is advanced over the shaft 13 and is pressed against the exterior of the patient's abdominal wall 11 to secure the gastrostomy catheter within the abdominal and stomach walls. The abdominal wall 11 and the stomach wall 12 are secured together at several locations by means of T-fasteners 18 which are disposed within the interior of the stomach. Sutures 19, which are secured by one end to each of the T-fasteners, pass through the abdominal and gastric-walls 11 and 12, a padded retention element, such as a cotton pledget 20 shown, and a nylon washer or button 21 disposed on the exterior of the abdominal wall 11. The sutures 19 may be knotted several times or crimps (not shown) may be employed to secure the buttons 21 against each of the pledgets 20 with sufficient pressure to hold the stomach against the wall of the abdomen.

The multiarm adapter 16 has an arm 22 which is adapted to receive nutrients and the like in fluid form from a source such as a syringe (not shown) and deliver such fluids through an inner lumen 23 within the catheter shaft 13 and out a port 24 in the distal end thereof to the interior of the patient's stomach. Arm 25 is adapted to receive medication in fluid form and deliver the fluids through the lumen 26 to a port 27 in the distal end of the catheter shaft 13. Alternatively, lumens 23 and 26 may be a single lumen. Arm 28 is adapted to receive an inflation device (not shown) and is in fluid communication with the balloon 14 through lumen 29.

Figure 7:
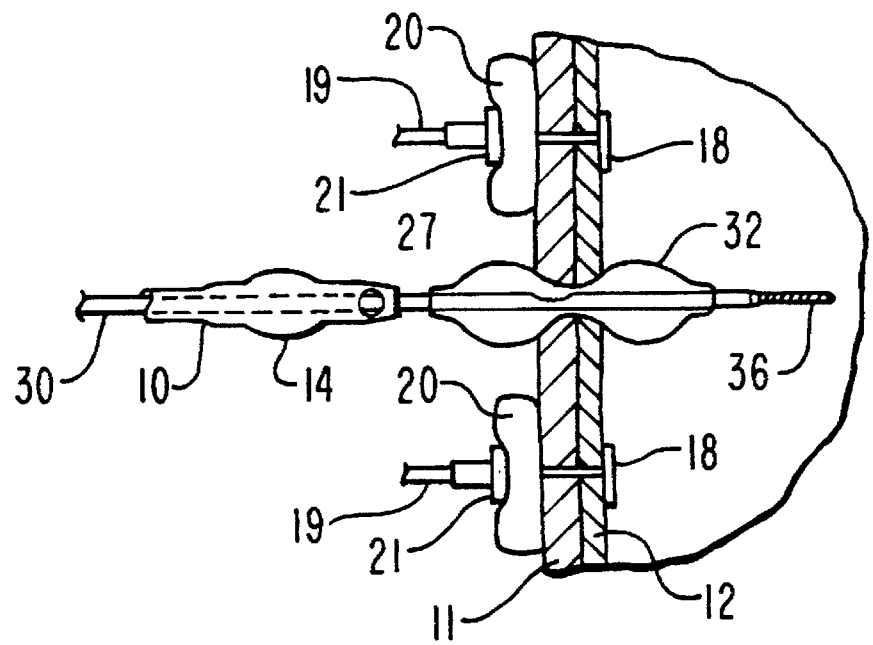
FIGS. 7–9 illustrate the insertion of the catheter assembly shown in FIG. 5 into a patient's stomach.
Figure 8:
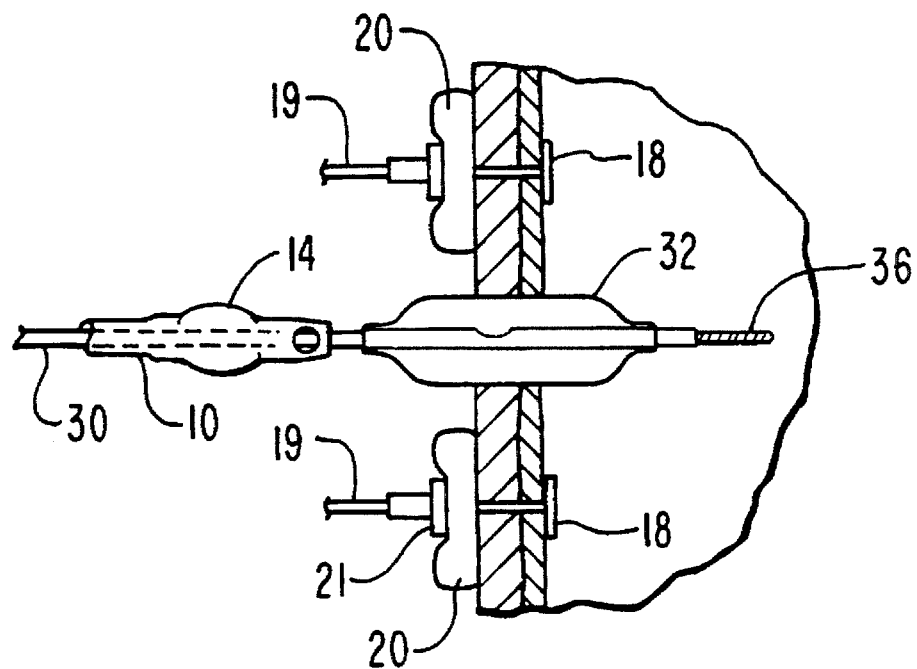
Figure 9:
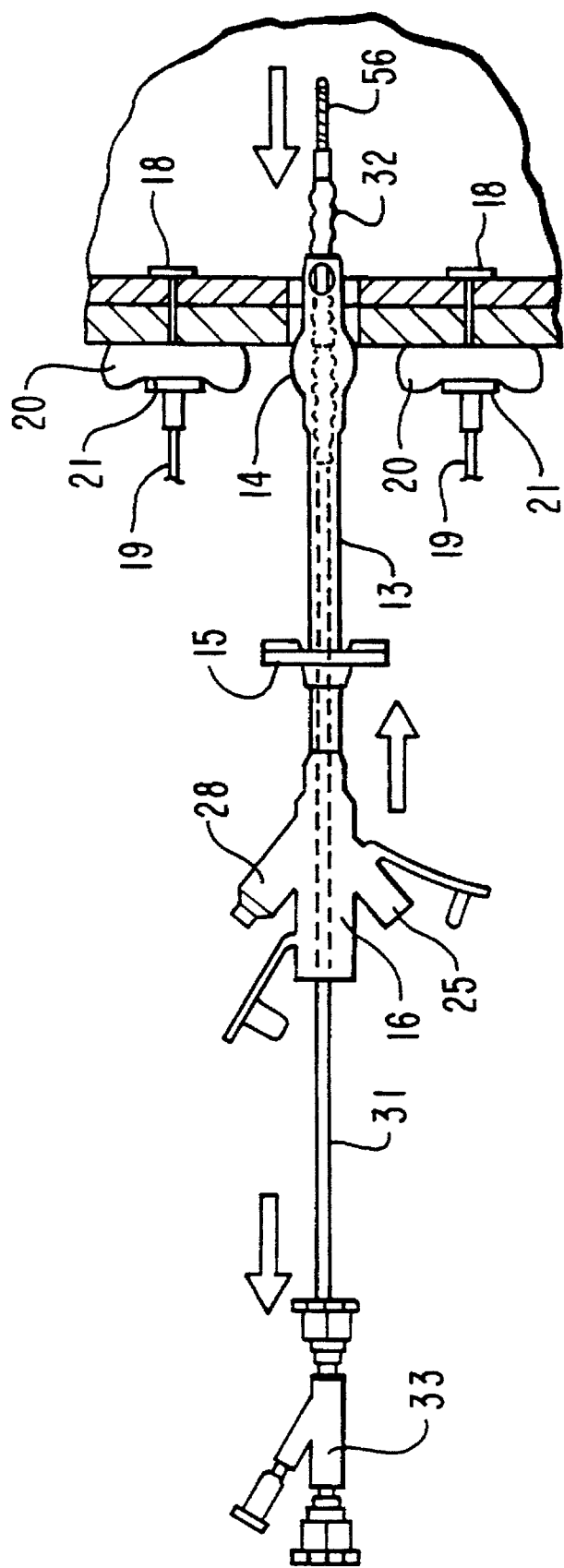

The gastrostomy catheter 10 is inserted through the passageway 17 in abdominal and stomach walls 11 and 12 with the aid of a dilatation catheter 30 as shown in FIGS. 7–9.

Figure 3:
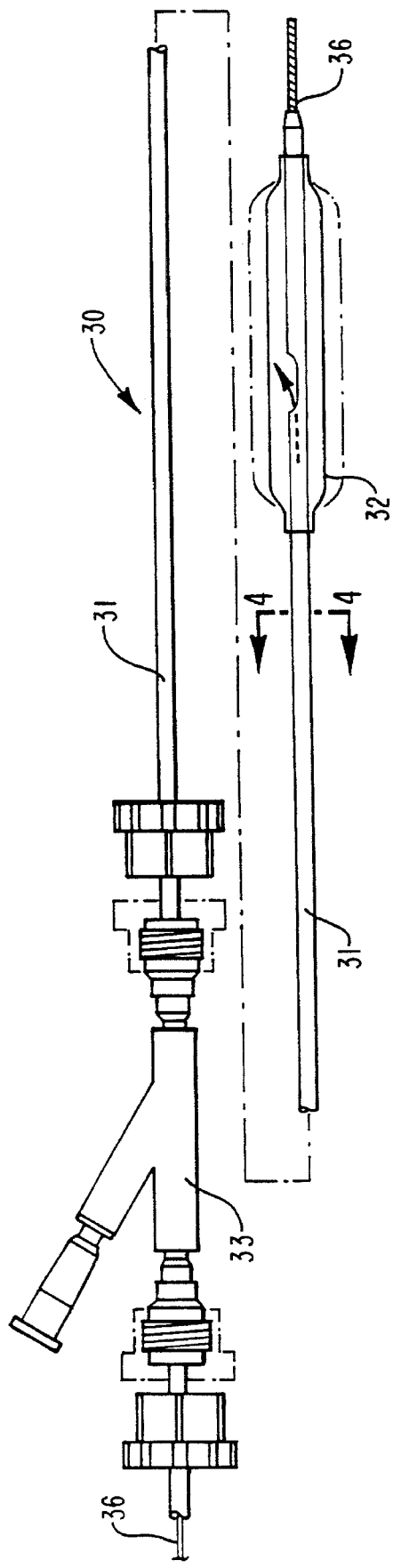
FIG. 3 is an elevational view of a dilatation catheter which embodies features of the present invention.
Figure 4:
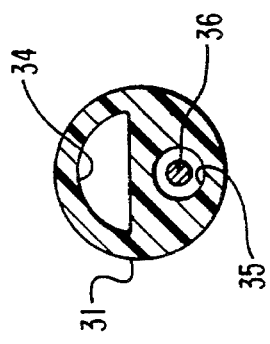
FIG. 4 is a transverse cross-sectional view of the dilatation catheter shown in FIG. 3 taken along the lines 4—4.
Figure 5:
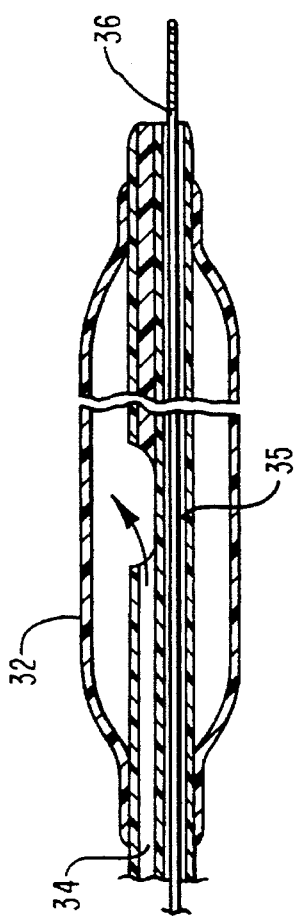
FIG. 5 is an enlarged cross-sectional view of a distal portion of the catheter shown in FIG. 3.

The dilatation catheter 30, as best shown in FIGS. 3–5, has an elongated shaft 31, a dilatation balloon 32 on a distal section thereof and a removable multiarm adapter 33, which is secured to the proximal end of the catheter shaft 31. The catheter shaft 31 has an inflation lumen 34 which extends therein from the proximal end of the catheter shaft to the interior of the balloon 32 and a guidewire receiving lumen 35 which extends from the proximal end to the distal end of the catheter shaft. The balloon member 32 is preferably formed of material which allows the balloon to be inflated to a desired size but which does not exhibit significant expansion beyond the desired size upon increased pressures e.g. it is relatively inelastic or noncompliant at its inflated diameter.

Figure 6:
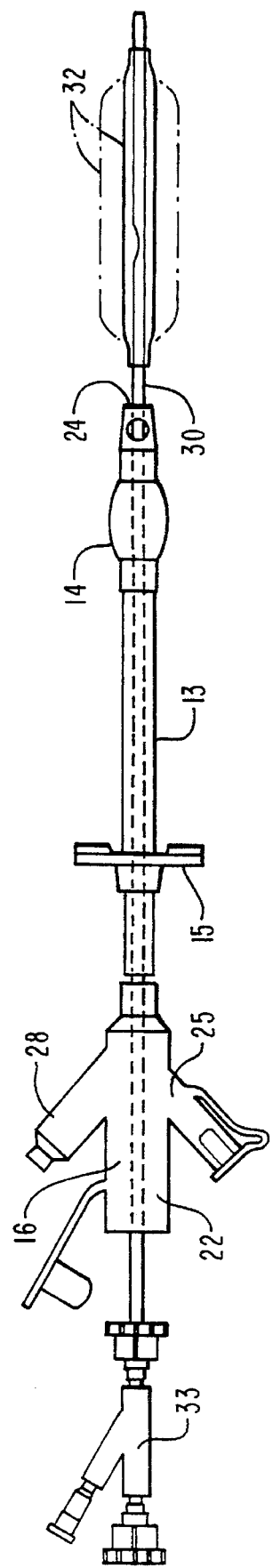
FIG. 6 is an elevational view of an assembly with the dilatation catheter shown in FIG. 3 disposed within an inner lumen of a gastrostomy catheter such as illustrated in FIG. 1.

FIG. 6 illustrates an assembly of the gastrostomy catheter 10 and the dilatation catheter 30 ready for insertion through passageway 17, with the dilatation catheter disposed within an inner lumen 23 of the gastrostomy catheter. To form the assembly the inner lumen 23 of the gastrostomy catheter 10 is lubricated with a suitable sterile lubricant, e.g. mineral oil, and then the proximal end of the dilatation catheter 30, with the adapter 33 removed, is inserted into the inner lumen 23 of the gastrostomy catheter through its distal end and advanced therein until the proximal end of the dilatation catheter extends out the arm 22 of the gastrostomy catheter. The dilatation balloon 30 should extend completely out of the port 24 in the distal end of the gastrostomy catheter 10 to ensure the complete inflation thereof. The adapter 33 may then be mounted onto the proximal end of the catheter shaft 31 and secured thereto by tightening collar 37.

To prepare the site on the patient's abdomen for insertion of the gastrostomy catheter 10, the patient's stomach is filled with air to displace the overlying bowel gas and the site is selected fluoroscopically to avoid the patient's liver, small bowel and colon. The three or four sites for T-fastener placement are marked on the exterior of the abdomen about the region chosen for gastrostomy catheter placement in the shape of an equilateral triangle (for three T-fastener sites) or a square (for four T-fastener sites). After prepping and draping, the skin, subcutaneous tissues and peritoneal lining are liberally anesthetized with a 1% procaine (Xylocaine®) and a nick is made through the skin at each of the T-fastener sites.

An introducer needle (e.g. 17 gage) preloaded with a T-fastener 18 is advanced through the anterior abdominal wall 11 through the nicks at a T-fastener site and then given a rapid thrust of 2–5 cm to ensure that the introducer needle passes completely through the gastric wall 12 and into the gastric lumen. The gastric wall tends to form an inwardly projecting tent-like structure when the distal end of the needle is pressed against the exterior thereof without penetration, but by providing a quick thrust, the sharp distal tip of the needle easily passes through the gastric wall. Air is aspirated with a syringe attached to the introducer needle to confirm that the distal tip of the needle is within the interior of the stomach. The syringe is removed from the needle and a rod is passed through the needle from its proximal end to push T-fastener 18 disposed within the needle lumen into the interior of the stomach. The suture 19 attached to the T-fastener extends out of the abdominal wall 11. The introducer needle is then removed and the suture secured to the T-fastener is withdraw., pulling the anterior gastric wall and omentum snugly against the anterior abdominal wall. The pledget 20 and the button 21, through which the suture 19 is threaded, are slid along the suture and urged against the abdominal surface and then the suture 19 is tied in several knots (5 or more is preferred) to hold the button 21 against the pledget 20 with sufficient pressure to hold the T-fastener 18 snugly but not tightly against the stomach wall 12 as shown in FIG. 1. A suitable T-fastener system is the Brown-Mueller T-fastener set available from Medi-tech (Boston Scientific Corp of Watertown, Mass.). Other suitable systems are commercially available.

The site for inserting the gastrostomy catheter 10 into the patient's stomach is prepared in essentially the same manner as the sites for inserting the T-fasteners 18. The skin, the subcutaneous tissues and the peritoneum are liberally anesthetized with a 1% procaine and then a small incision, e.g. 10–12 mm in length, is made parallel to the major branches of the superior epigastric arteries. An introducer needle (e.g. 18 gage puncture needle) is advanced through the center of the incision into the interior of the stomach and a syringe is attached to the needle to aspirate air to ensure proper placement within the interior of the stomach. A suitable guidewire 36 (e.g. a 0.038" J-tip guidewire) is passed through the lumen of the needle into the interior of the stomach and allowed to loop liberally within the stomach to protect against accidental dislodgement of the guidewire. The introducer needle is then withdrawn from the abdominal and gastric walls 11 and 12 and the passageway or track 17 formed in the abdominal and stomach walls by the introducer needle is predilated by passing a plurality of catheter type dilators, e.g. first an 8 french catheter and then a 12 french catheter, over the in-place guidewire 36 to facilitate the advancement of the dilatation catheter 30 through the track 17.

The gastrostomy catheter 10 is preloaded onto the shaft 31 of the dilatation catheter 30 by removing the adapter 33 on the dilatation catheter and advancing the gastrostomy catheter over the dilatation catheter (or vice versa) until the dilatation balloon 32 extends completely out of the distal end of the gastrostomy catheter and then the assembled catheters are advanced over the in-place guidewire 36 until the balloon 32 on the dilatation catheter 30 extends through the passageway 17 across both the abdominal wall 11 and the stomach wall 12. The adapter 33 is remounted onto the proximal end of the dilatation catheter 30 and then by passing the shaft 31 into the distal end of the adapter and tightening the cap 32 onto the distal of the adapter (see FIG. 31 dilatation balloon 32 is inflated to dilatation pressures (e.g. 12–15 atm.) to dilate the track 17 sufficiently to allow the gastrostomy catheter 10 to pass easily through the passageway without applying stress to the stomach wall which might tear the wall away from the T-fastener 18. The balloon 32 is preferably inflated with radiopaque liquid so that the expansion of the balloon can be monitored fluoroscopically. In the initial stages of the dilatation as shown in FIG. 7, the portion of the balloon 32 within the fascia of the abdominal wall does not expand as much as the rest of the tissue through which the balloon extends and it forms a waist 37 which is readily observed fluoroscopically. The balloon 32 is inflated one or more times to its dilatation diameter within the passageway 17 until the waist 37 disappears as shown in FIG. 8. It is important that the passageway 17 be properly dilated so that there is no excessive force applied to the stomach wall when pushing of the gastrostomy catheter 10 through the passageway which might cause the T-fasteners to tear through the wall of the stomach. For gastrostomy and other types of catheters within the size range of about 14–30 French, the passageway 17 should be expanded to at least about 1 cm to ensure minimum forces on the stomach wall 12.

After the dilatation of the passageway 17 is complete, the balloon 32 on the dilatation catheter 30 is deflated and the gastrostomy catheter 10 is advanced over the dilatation catheter 30 as shown in FIG. 9 until the balloon 14 on the gastrostomy catheter is well within the interior of the stomach. The balloon 14 is inflated to the desired size and then the gastrostomy catheter 10 is withdrawn through the passageway 17 until the inflated balloon 14 is pulled snugly against the stomach wall 12. The dilatation catheter 30 and the guidewire 36 are removed after confirming that the balloon 14 is properly positioned within the stomach. The external retention ring 15 on the shaft 13 of the catheter 10 is pushed against the exterior of the abdominal wall 11 as depicted in FIG. 1 to effectively secure the gastrostomy 10 within the stomach. Care must be exercised to avoid excessive pressure by the external retention means, i.e. balloon 14, against the gastric wall 12, because high pressure over a long term can cause tissue necrosis. After the gastrostomy catheter 10 has been in place for about 10–14 days there is relatively sound bond between the abdominal and stomach walls 11 and 12, so the sutures 19 connected to the T-fasteners 18 may be severed at the exterior of the abdominal wall 11 releasing the T-fasteners 18 into the stomach. The released fasteners 18 ultimately pass harmlessly through the gastrointestinal system of the patient.

The dilatation catheter 30 typically has an overall length of about 12 to about 40 inches/30.4–102 cm) and a shaft diameter of about 3–8 French (1–2.6 mm) to facilitate passages through inner lumen 23 of gastrostomy catheter 10. The balloon has an inflated diameter of about 5 to about 15 mm and a length of about 1 to about 15 cm, preferably about 8–12 cm. The dimensions of the dilatation catheter depend to a large extent upon the dimensions of the gastrostomy catheter to be used. The overall length of the dilatation catheter 30 must be great enough so that proximal end extends out the proximal end of the gastrostomy catheter and the balloon 32 extends completely out the distal end of the gastrostomy catheter.

The gastrostomy catheter 10 and the dilatation catheter 30 can be conveniently packaged together as a kit with the catheters either separate from one another or with the dilatation catheter 30 slidably disposed within the inner lumen 23 of the gastrostomy catheter as shown in FIG. 6. Ideally, the assembly of the gastrostomy catheter 10 and the dilatation catheter 30 are ready for mounting on a guidewire. Additional items which may be included in the kit include a guidewire, T-fasteners with attached sutures, suitable pledgets and buttons, an inflation device such as syringe, an introducer needle and the like. Other items used in the procedure of inserting and fixing the gastrostomy catheter 10 may also be included in the kit such as a vial of anesthetic, e.g. 1% procaine and a needle and syringe to use the anesthetic.

While the invention has been described herein primarily in terms of catheters adapted for stomach access, the enteric gastrostomy catheters may also provide jejunal access such as with the MIC Gastro-Enteric Tube and the MIC Jejunal Tube which are available from the assignee of the present application, Medical Innovations Corporation of Milpitas, Calif. Various modifications can be made to the invention without departing from the scope thereof. For example, the catheter shaft of the gastrostomy catheter is depicted in FIG. 2 as extruded or other wise formed into a unitary mass. However, the shaft can be formed from individual tubular elements which have been heat fused together. Other modifications and improvements to the invention will be apparent to those skilled in the art.

What is claimed is:

1. A gastrostomy catheter system comprising:
   (a) outer gastrostomy catheter means adapted for long-term placement through a patient's abdominal and stomach walls into the patient's stomach cavity, said gastrostomy catheter means comprising:
      (1) a gastrostomy tube having at least one lumen running the length of the gastrostomy tube and through which fluids may be introduced into the stomach cavity after the gastrostomy tube is in place; and
      (2) means for securing the gastrostomy tube in place relative to the abdominal and stomach walls, said securing means comprising first inflatable means for securing the gastrostomy tube against the stomach wall and slidable retention means for securing the gastrostomy tube against the abdominal wall so as to essentially prevent movement of the gastrostomy robe relative to either wall; and
   (b) inner dilatation catheter means for introducing the outer gastrostomy tube and the first inflatable means for securing the tube into the stomach cavity together with the dilatation catheter through an enlarged stoma formed by a second inflatable dilatation means, said dilatation catheter means being temporarily disposed in said lumen when introducing the gastrostomy tube and the first inflatable means for securing the tube in the stomach cavity, and thereafter being removable from said lumen to permit fluids to be introduced through the lumen into the stomach cavity and said dilatation catheter means comprising;
      (1) an elongated catheter shaft having a sufficient length so that when the catheter shalt is disposed in the lumen of the gastrostomy tube, a distal portion of the catheter shaft will extend beyond the lumen of the gastrostomy tube and a proximal portion of the catheter shaft will be accessible at the opposite end of the lumen of the gastrostomy tube so as to permit removal of the catheter shaft after introducing the gastrostomy tube and first means for securing the tube in the stomach cavity; and
      (2) a second inflatable dilatation means at said distal portion of the elongated catheter shaft and having an inflatable diameter larger than the first inflatable securing means, for radially expanding a passageway formed through the abdominal and stomach walls as the second inflatable dilatation means is inflated so that the passageway will thereafter accommodate introduction therethrough of the gastrostomy tube and first inflatable means for securing the tube, said dilatation means being located at the distal portion of the catheter shaft and being in fluid communication therewith so as to be inflatable by fluid communicated through the catheter shaft to the dilatation means.

2. The system of claim 1 wherein the second inflatable dilatation means is an inflatable member formed of relatively inelastic plastic materials.

3. The system of claim 2 wherein the dilatation member comprises a balloon that has a length of about 1 to about 15 cm and is adapted to have a maximum inflated diameter of about 5 to about 15 mm.

4. The system of claim 2 wherein the inflatable member is formed from a material selected from the group consisting of polyvinyl chloride, polyethylene, polyethylene, polyethylene terephthalate and polyolefinic ionomer.

5. The system of claim 1 wherein the gastrostomy tube comprises a guidewire lumen extending therein and an adapter releasably secured to a proximal end of the gastrostomy tube and which has an arm adapted for connection to a source of inflation fluid.

6. The system of claim 5 wherein the second inflatable dilatation means comprises an inflatable balloon formed of relatively inelastic material.

7. The system of claim 6 wherein the elongated catheter shaft of the dilatation catheter means comprises an inflation lumen extending therein which is in fluid communication with the interior of the inflatable balloon.

8. The system of claim 1 wherein the slidable retention means for securing the gastrostomy tube is comprised of an external retention member which is adapted to slide along said tube to the exterior of the patient's abdominal wall.

9. The system of claims 1 or 8 wherein the first inflatable means for securing the gastrostomy tube comprises an internally inflatable member.

10. The system of claim 9 further comprising means for inflating the inflatable, member.

11. The system of claim 1 further comprising means for holding together the patient's abdominal wall and stomach wall.

12. The system of claim 11 wherein the holding means is comprised of at least one T-fastener having an elongated suture fixed thereto with an end adapted to be passed through the patient's stomach and abdominal walls and tied outside of the patient.

13. The system of claim 1 further comprising means to inflate the second inflatable dilatation means of the dilatation catheter means.

* * * * *

UNITED STATES PATENT AND TRADEMARK OFFICE
CERTIFICATE OF CORRECTION

PATENT NO. : 5,458,583                                   Page 1 of 2

DATED      : October 17, 1995

INVENTOR(S): GWYN F. McNEELY et al.

It is certified that error appears in the above-identified patent and that said Letters Patent is hereby corrected as shown below:

Title page, column 2, item {57], line 20, after "catheter" insert --is--
Column 1, line 13, "patient's" should be --patients--
Column 1, line 15, "patient's" should be --patients--
Column 1, line 18, "esophagus" should be --esophagi--
Column 1, line 24, "of" should be --as--
Column 1, line 26, "well known" should be --well-known--
Column 1, line 28, delete "of"
Column 1, line 28, "techniques" should be --technique--
Column 1, line 37, "," should be --;--

Column 2, line 21, delete "over"
Column 2, line 22, delete "the"
Column 2, line 26, delete "that"
Column 2, line 43, "Preferable" should be --Preferably--
Column 2, line 58, delete "thereto"
Column 3, line 1, "can not" should be --cannot--
Column 3, line 11, "fascia" should be --fasciae--
Column 3, line 17, after "inflation" insert --occurrence--
Column 3, lines 18-19, "dilatation balloon" should be --dilatated balloon--
Column 3, line 27, "dilatation balloon" should be --dilatated balloon--
Column 3, line 32, after "catheter" insert --,--
Column 4, line 20, "fictionally" should be --frictionally--
Column 4, line 33, "gastric-walls" should be --gastric walls--
Column 5, line 31, "gage" should be --gauge--
Column 5, line 49, "withdraw.," should be --withdrawn,--
Column 6, line 1, "gage" should be --gauge--
Column 6, lines 13 and 14, "french cather" should be --French catheter--
Column 6, lines 29-30, "(see FIG. 31" should be --(see FIG. 3)--

UNITED STATES PATENT AND TRADEMARK OFFICE
CERTIFICATE OF CORRECTION

PATENT NO. : 5,458,583

DATED : October 17, 1995

INVENTOR(S) : GWYN G. McNEELY et al.

It is certified that error appears in the above-identified patent and that said Letters Patent is hereby corrected as shown below:

Column 6, line 38, "fascia" should be --fasciae--
    Column 6, line 43, "waist 37" should be --waist 27--
    Column 6, line 46, delete "of the"
    Column 7, line 4, after "there is" insert --a--
    Column 7, line 8, after "wall 11" insert --,--
    Column 7, line 14, "passages" should be --passage--
    Column 7, line 19, after "so that" insert --the--
    Column 7, line 32, "such as syringe" should be --such as a syringe--
    Column 7, line 47, "other wise" should be --otherwise--
    Column 9, line 5, "inflatable, member." should be --inflatable member--

Signed and Sealed this

Twenty-ninth Day of July, 1997

Attest:

BRUCE LEHMAN

Attesting Officer

Commissioner of Patents and Trademarks